United States Patent [19]
Mak

[11] Patent Number: 4,713,332
[45] Date of Patent: Dec. 15, 1987

[54] T CELL SPECIFIC CDNA CLONE

[75] Inventor: Tak W. Mak, Toronto, Canada

[73] Assignee: The Ontario Cancer Institute, Toronto, Canada

[21] Appl. No.: 577,526

[22] Filed: Feb. 6, 1984

Related U.S. Application Data

[63] Continuation-in-part of Ser. No. 570,694, Jan. 13, 1984.

[51] Int. Cl.$^4$ .................... C12P 21/02; C12P 19/34; C12N 15/00; C07H 15/12
[52] U.S. Cl. ........................................ 435/70; 435/91; 435/172.3; 536/27; 935/12; 935/15
[58] Field of Search ............... 536/27; 435/68, 172.3, 435/317; 935/6, 9, 12, 22, 27

[56] References Cited

PUBLICATIONS

Berzofsky, 1983, "Promising Clues to Reception Genes and Molecules", *Immunology Today*, vol. 4, pp. 299–301.
Hood et al., 1978, *Immunology*, Benjamin/Cummings Publishing Co., Menlo Park, pp. 7–8.
Kappler et al., 1983, "The Mouse T Cell Receptor: Comparison of MHC-Restricted Receptors on Two T Cell Hybridomas", *Cell*, vol. 34, 727–737.
Acuto et al., 1983, "The Human T Cell Receptor: Appearance in Ontogeny and Biochemical Relationship of α-andβ-Subunits . . .", *Cell*, vol. 34, 717–726.
Marx, 1983, "Likely T Cell Receptor Gene Cloned", *Science*, vol. 221, (Sep. 23), pp. 1278–1279.
Malissen et al., 1984, "Mouse T Cell Antigen Receptor: Structure and Organization of Constant and Joining Gene Segments Encoding B-Polypeptide", *Cell*, vol. 37, 1101–1110.
Kronenberg et al., 1983, "Finding the T-Cell Antigen Receptor: Past Attempts and Future Promise", *Cell*, vol. 34, 327–329.
McIntyre et al., 1983, "The Mouse T Cell Receptor: Structural Heterogeneity of Molecules of Normal T Cells Defined by Xenoantiserum", *Cell*, vol. 34, 739–746.

*Primary Examiner*—Thomas G. Wiseman
*Assistant Examiner*—Thomas D. Mays
*Attorney, Agent, or Firm*—Ridout & Maybee

[57] ABSTRACT

The invention provides a nucleic acid having a sequence which encodes a polypeptide that is at least part of a T cell antigen receptor. This encoded sequence is about 936 nucleotides in length and preferably is a human T cell antigen receptor. The nucleic acid sequence of one embodiment of the invention is shown in FIG. 3.

The nucleic acid sequence may be used as a probe to determine whether an unknown cell, e.g., a tumor cell, is a T cell.

Polypeptides encoded by the nucleic acid sequence include about 312 amino acids and are at least part of a T cell antigen receptor. They include at least one sequence which over 21 contiguous amino acids has greater than about 35% homology with mouse and human immunoglobin λ light chains.

Antibody to the polypeptide may be prepared and used to identify T cell antigen receptor and to determine whether an unknown cell, e.g., a tumor cell, is a T cell.

24 Claims, 7 Drawing Figures

```
                                          MetAspSerTrpThrPheCysCysValSerLeuCysIleLeuValAlaLysHis   18
CTGGTCTAGAATATTCCACATCTGCTCTCACTCTGCCATGGACTCCTGGACCTTCTGCTGTGTGTCCCTTTGCATCCTGGTAGCGAAGCA
    10        20        30        40        50        60        70        80        90

ThrAspAlaGlyValIleGlnSerProArgHisGluValThrGluMetGlyGlnGluValThrLeuArgCysLysProIleSerGlyHis   48
TACAGATGCTGGAGTTATCCAGTCACCCCGCCATGAGGTGACAGAGATGGGACAAGAAGTGACTCTGAGATGTAAACCAATTTCAGGCCA
    100       110       120       130       140       150       160       170       180

AsnSerLeuPheTrpTyrArgGlnThrMetMetArgGlyLeuGluLeuLeuIleTyrPheAsnAsnAsnValProIleAspAspSerGly   78
CAACTCCCTTTTCTGGTACAGACAGACCATGATGCGGGGACTGGAGTTGCTCATTTACTTTAACAACAACGTTCCGATAGATGATTCAGG
    190       200       210       220       230       240       250       260       270

MetProGluAspArgPheSerAlaLysMetProAsnAlaSerPheSerThrLeuLysIleGlnProSerGluProArgAspSerAlaVal   108
GATGCCCGAGGATCGATTCTCAGCTAAGATGCCTAATGCATCATTCTCCACTCTGAAGATCCAGCCCTCAGAACCCAGGGACTCAGCTGT
    280       290       300       310       320       330       340       350       360

TyrPheCysAlaSerSerPheSerThrCysSerAlaAsnTyrGlyTyrThrPheGlySerGlyThrArgLeuThrValValGluAspLeu   138
GTACTTCTGTGCCAGCAGTTTCTCGACCTGTTCGGCTAACTATGGCTACACCTTCGGTTCGGGGACCAGGTTAACCGTTGTAGAGGACCT
    370       380       390       400       410       420       430       440       450

AsnLysValPheProProGluValAlaValPheGluProSerGluAlaGluIleSerHisThrGlnLysAlaThrLeuValCysLeuAla   168
GAACAAGGTGTTCCCACCCGAGGTCGCTGTGTTTGAGCCATCAGAAGCAGAGATCTCCCACACCCAAAAGGCCACACTGGTGTGCCTGGC
    460       470       480       490       500       510       520       530       540

ThrGlyPhePheProAspHisValGluLeuSerTrpTrpValAsnGlyLysGluValHisSerGlyValSerThrAspProGlnProLeu   198
CACAGGCTTCTTCCCCGACCACGTGGAGCTGAGCTGGTGGGTGAATGGGAAGGAGGTGCACAGTGGGGTCAGCACAGACCCGCAGCCCCT
    550       560       570       580       590       600       610       620       630
```

```
                                      MetAspSerTrpPheCysCysValSerLeuCysIleLeuValAlaLysHis   18
CTGGTCTAGAATATTCCACATCTGCTCTCACTCTGCCATGGACTCCTGGACCTTCTGCTGTGTCCCTTGCATCCTGGTAGCGAAGCA
         10        20        30        40        50        60        70        80        90

ThrAspAlaGlyValIleGlnSerProArgHisSerProArgHisSerProIleSerGlyHis                            48
ThrAspAlaGlyValIleGlnSerProArgHisSerProIleSerGlyHis                                        48
TACAGATGCTGGAGTTATCCAGTCCAGTCCAGTTATCCAGTCCAGTGACAAGAAGTGACTCTGAGATGTAAACCAATTTCAGGCCA
        100       110       120       130       140       150       160       170       180

AsnSerLeuPheTrpTyrArgGlnThrMetMetArgGlyLeuGluLeuLeuIleTyrPheAsnAsnValProIleAspSerGly      78
CAACTCCCTTTTCTGGTACAGACAGACCATGATGCGGGACTGGAGTTGCTCATTTACTTTAACAACGTTCCGATAGATTCAGG
        190       200       210       220       230       240       250       260       270

MetProGluAspArgPheSerAlaLysMetProAsnAlaSerPheThrLeuLysIleGlnProSerGluProArgAspSerAlaVal   108
GATGCCCGAGGATCGATTCTCAGCTAAGATGCCTAATGCCATCATTCTCCACTCTGAAGATCCAGCCCTCAGAACCCAGGACTCAGCTGT
        280       290       300       310       320       330       340       350       360

TyrPheCysAlaSerSerPheSerThrCysSerAlaAsnTyrGlyTyrThrPheGlySerGlyThrArgLeuThrValValGluAspLeu 138
GTACTTCTGTGCCAGCAGTTCTCGACCTGTTCGGCTAACTATGGCTACACCTTCGGTTCGGGGACCAGGTTAACCGTTGTAGAGGACCT
        370       380       390       400       410       420       430       440       450

AsnLysValPheProProGluAlaValPheGluProSerGluAlaIleSerHisThrGlnLysAlaThrLeuValCysLeuAla      168
GAACAAGGTGTTCCCACCCGAGGTCGCTGTGTTTGAGCCATCAGAAGCAGAGATCTCCCACACCCAAAAGGCCACACTGTGCCTGGC
        460       470       480       490       500       510       520       530       540

ThrGlyPhePheProAspHisValGluLeuSerTrpTrpValAsnGlyLysGluValHisSerGlyValSerThrAspProGlnProLeu 198
CACAGGCTTCTTCCCCGACCACGTGGAGCTGAGCTGGTGGGTGAATGGGAAGGAGGTGCACAGTGGGGTCAGCAGACCCCAGCCCCT
        550       560       570       580       590       600       610       620       630
```

Figure 3a

```
LysGluGlnProAlaLeuAsnAspSerArgTyrCysLeuSerArgLeuArgValSerAlaThrPheTrpGlnAsnProArgAsnHis 228
CAAGGAGCAGCCCGCCCTCAATGACTCCAGATACTGCCTGAGCAGCCGCCTGAGGGTGTCAGCCACCTTCTGGCAGAACCCCGCAACCA
       640        650        660        670        680        690        700        710        720

PheArgCysGlnValGlnPheTyrGlyLeuSerGluAsnAspGluTrpThrGlnAspArgAlaLysProValThrGlnIleValSerAla 258
CTTCCGCTGTCAAGTCCAGTTCTACGGGCTCTCGGGAGAATGACGAGTGGACCCAGGATAGGGCCAAACCCGTCACCCAGATCGTCAGCGC
       730        740        750        760        770        780        790        800        810

GluAlaTrpGlyArgAlaAspCysGlyPheThrSerValSerTyrGlnGlnGlyValLeuSerAlaThrIleLeuTyrGluIleLeuLeu 288
CGAGGCCTGGGGTAGAGCAGACTGTGGCTTTACCTCGGTGTCCTACCAGCAAGGGGTCCTGTCTGCCACCATCCTCTATGAGATCCTGCT
       820        830        840        850        860        870        880        890        900

GlyLysAlaThrLeuTyrAlaValLeuValLeuMetAlaMetValLysArgLysAspPhe*** 312
AGGGAAGGCCACCCTGTATGCTGTGCTGGTCCTGATGGCCATGGTCAAGAGAAAGGATTTCTGAAGGCAGCCCTGAA
       910        920        930        940        950        960        970        980        990

GTGGAGTTAGGAGCTTCTAACCCGTCATGGTTCAATACACATTCTCTTTTTGCCAGCGGCTTCTGAAGAGCTGCTCCTCCACCTCTCGCATC
       1000       1010       1020       1030       1040       1050       1060       1070       1080

CCAATAGATATCCCCCTATGTGCATGCACACCTGCACACTCACGGGCTGAAATCTCCCTAACCCAGGGGAC
       1090       1100       1110       1120       1130       1140       1150
```

Frame 3
Frame 2
Frame 1

```
  1   MDSWTFCCVS---LCILVAKHTDAGVIQ-SPRHEVTEMGQEVTLRCKPISG--HNSLFW-YRQT-MMRGLELLIYFNNN-V      YT35
      * ** |||* ** |* | *|**|**|    *|* **|**|    |* |||| *  |||| |*||||||***|||||*|
 -19  MA-WTSLILSLLALCS-GASSQ-AVVTQESA--LTTSPGGTVILTCRSSTGAVTTSNYANWIQEKPDHLFTGLIGGTSNRA     Murine λ light chain
      ← Signal Peptide →                                                      ← HVR1 →

PKAN-PTVTLFPPS                Human λ light chain
                                                                 *|  * **|****
  1   PIDDSGMPEDRFSAKMPNASFSTLKIQPSEPRDSAVYFCASSFSTCSANYGYTFGSGTRLTVVEDLN-KVFPPEVAVFEPS      YT35
       *|* ***| ||  |  ** ||     *|*****     *  ||** **||**|  || ** |  | * *|
 73   P-----GVP-VRFSGSLIGDKAA-LTITGAQTEDDAMYFCALWF----RNH-FVFGGGTKVTVL--GQPKST-PTLTVFPPS    Murine λ light chain
 58                                             ← HVR3 →    ← J Region →

14   SEELQA-NKATLVCLISDFYPGAVTVAWKADGSPVKAGVETT-KPSK-QS--N-NKYAASSYL--SLTPEQ-WKSHRSYSC    Human λ light chain
      *|| |******** ||** |* | *    *|*  **| ||*|**|  *| ***|*** |||* ||
153   EAEISHTQKATLVCLVCLATGFFPDHVELSWWVNGKEVHSGVSTDPQPLKEQPALNDSRYCLSSRLRVSATFWQNPRNH--FRC    YT35
      *||  |  ******||||******** | |** |* ||*|* * |** *  * |*|* *
125   SEEL-KENKATLVCLISNFSPSGVTVAWKANGTPITQGVDTS-NPTKE--G----NKFMASSFLHL--TSDQ-WRSHNSFTC   Murine λ light chain 86   QVTHEGSTVEKTVAPTECS     Human λ light chain
      **| *   | |  |||||
232   QVQFYGLS-ENDEWTQDDRAKPVTQIVSAEAWGRADCGFTSVSYQQGVLSATILYEILLGKATLYAVLVSALVLMAMVKRKDF  YT35
      **|   |     |
197   QVTHEGDTVEKSLSPAECL     Murine λ light chain
```

T CELL SPECIFIC CDNA CLONE

This application is a continuation-in-part of my U.S. Ser. No. 570,694 filed Jan. 13, 1984 and entitled T CELL SPECIFIC CDNA CLONE.

T (thymus derived) cells, like B cells, recognize specific antigens. This recognition is essential for activation of T cells, which have at least two major functions in the immune system. They kill cells that appear foreign, such as cells that have been infected with viruses and carry viral antigens and they regulate other immune responses, including antibody production by B cells (H. R. Green et al., (1983) Ann. Rev. Immunol. 1, 439–461; P. C. Kung et al., (1983) Intl. J. Dermatol. 22, 67–76).

Antigen recognition is thought to be mediated through a receptor on T cells. Molecular and biochemical characterization of the T cell antigen receptor should clear up many of the mysteries concerning T cell recognition of antigen and should help in attaining a better understanding of the myriad interactions between the immune cells and their targets, and consequently, a better understanding of the regulation of immune responses.

In spite of extensive efforts, progress in characterizing the T cell antigen receptor during the past two decades has been slow (J. J. Marchalonis, (1982) Immunol. Today 3, 10–12; M. Kronenberg et al., (1983) Cell. 34, 327–329). Recently several groups of investigators have, however, produced murine monoclonal antibodies that may recognize T cell surface proteins with the predicted characteristics of the antigen receptor (J. L. Marx, (1983) Science 221, 444–446). These antibodies were produced by immunizing mice with cell lines of cloned T cells; and the antibodies react with only the cells used to elicit the antibody production. Immunochemical studies in man (S. C. Meuer et al., (1983) J. Exp. Med. 157, 705–719; S. C. Meuer et al., (1983) J. Exp. Med. 158, 988–993; R. D. Bigler et al., (1983) J. Exp. Med. 158, 1000–1005; A. Oreste et al., (1983) Cell. 34, 717–726; J. Kappler et al., (1983) Cell. 35, 295–302; S. C. Meuer et al., (1983) Science 222, 1239–1242) and in rodents (K. Haskins et al., (1983) J. Exp. Med. 157, 1149–1161; P. Marrack et al., (1983) J. Exp. Med. 158, 1635–1646; B. W. McIntyre and J. P. Allison, (1983) Cell 34, 739–746; J. Kappler et al., (1983) Cell. 34, 727–734) suggest that the putative T cell antigen receptor is a molecule composed of two different polypeptide chains with molecular weights of approximately 40,000 and 45,000 daltons, respectively. Under nonreducing conditions the T cell receptor molecule is a disulfide-linked heterodimer with a molecular weight of 85,000 to 90,000 daltons. Peptide mapping analysis in the murine system suggests that the T cell receptor protein contains a variable and a constant region. However, these studies have provided no information concerning the protein or nucleotide sequences.

Recently, there have appeared several reports that Stephen Hedrick at the National Institutes of Allergy and Infectious Diseases (NIAID) and Mark Davis, until recently with NIAID and now at Stanford Medical School, have prepared cDNA from T cell mRNA which may encode a T cell receptor protein (J. L. Marx, (1983) Science 221, 1278–1279; J. Berzofsky, (1983) Immunol. Today 4, 299–301). These reports suggest that the encoded protein may contain features in common with the variable and constant regions of immunoglobulin chains. These reports, however, do not contain information concerning: (a) the amino acid sequence of the putative T cell receptor protein; (b) the precise size or nucleotide sequence of the cDNA prepared; (c) the origin of the T cells studied (presumably murine cells); (d) the experimental protocols followed; and (e) data concerning the cDNA or the protein. Therefore, these reports would not enable one of ordinary skill in the art to reproduce or confirm the conjectured results. In addition, there are no suggestions concerning possible uses of cDNA encoding the receptor protein or of the receptor protein.

This invention relates to the isolation and detailed molecular characterization of a human T cell antigen receptor protein and the gene which encodes it. The invention also concerns a method of isolating and screening for the receptor gene, the nucleotide sequence of the gene, the amino acid sequence of the protein encoded by the gene and uses of the nucleotide sequence and the protein including the determination whether an unknown cell is a T cell.

The present invention provides a cloned cDNA which is specific for human T lymphoid cells. The message was found to be expressed in human and mouse T lymphoblasts, thymocytes and phytohaemmaglutinin stimulated T lymphocytes. Analysis of the amino acid sequence deduced from the nucleotide sequence indicates that its size and the relative positions of the cysteine residues are similar to the light chain of mouse and human immunoglobulin molecules. The nucleotide sequence of the cDNA of the invention contains a stretch of extensive homology to the variable, joining and constant regions of the light chain proteins in both human and mouse immunoglobulin. These features indicate that the cDNA clone corresponds to a message that specifies part of the human T cell receptor.

A particular description of the invention follows with reference being made to the drawings in which.

The method whereby the cDNA clone was obtained utilized the human leukemic T cell line MOLT-3 (Nagasawa, K. and Mak, T. W. (1982) Cell Immunol 71, 390–403). This cell line is known to contain T cell specific antigens. Messenger RNA was isolated from MOLT-3 cells by oligo-(dT)-cellulose column chromatography, and cDNA was synthesized using the method of Land et al ((1981) Nucleic Acid Res. 9, 2251–2266). Using mRNA from MOLT-3 cells, double stranded cDNA was generated and inserted into the Bgl II site of the vector pFP502EB5 (Clark, S. P. and Mak, T. W. (1982) Nuclei Acid Res. 10, 3315–3330). After transfection into E. coli strain HB101, 10,000 independent cDNA clones were obtained. A random survey of 25 of these cDNA clones indicated that the lengths of the cDNA inserts were between 0.5 and 1.7 kb.

In order to screen for cDNA expressed either exclusively or preferentially in T cells, the cDNA clones were grouped on the basis of their relative levels of expression in MOLT-3 cells and the human B cell line HSC-58. Four of these clones, YT30, YT35, YT53 and YT76, were specific for MOLT-3 cells by Northern gel analysis. A single message of 1.3 kb was detected in MOLT-3 cells but not in HSC-58. To test if this message was specific for T cell lines in general, hybridization with RNA from the following cell lines were examined:

(a) T cell lines Jurkat and CEM(T)
(b) B cell lines RPM1 1788(B) and RPM1 3638(B)
(c) cells from a patient with B cell chronic lymphocytic leukemia
(d) the erythroleukemic cell line K562 and one obtained from H. Messner, Ontario Cancer Institute
(e) normal bone marrow cells
(f) bladder tumor cell line MGHU-1.

Figure 1A:
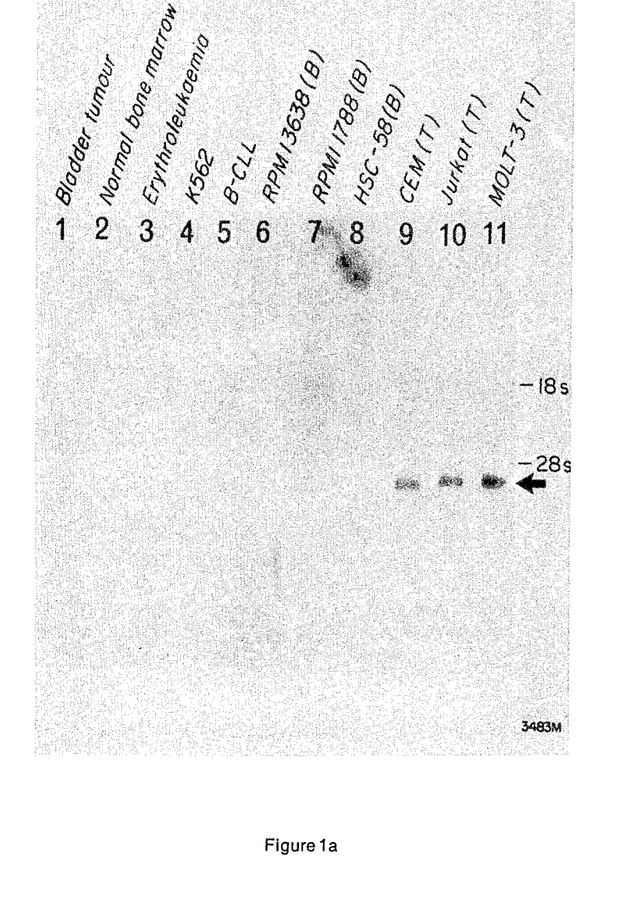
FIG. 1 is a Northern blot examination of T and non-T cell RNA for hybridization to clone YT35.

From FIG. 1a, it can be seen that this 1.3 kb message was expressed in all three T cell lines examined but was not expressed in any non-T cells or cell lines (arrow).

Figure 1B:
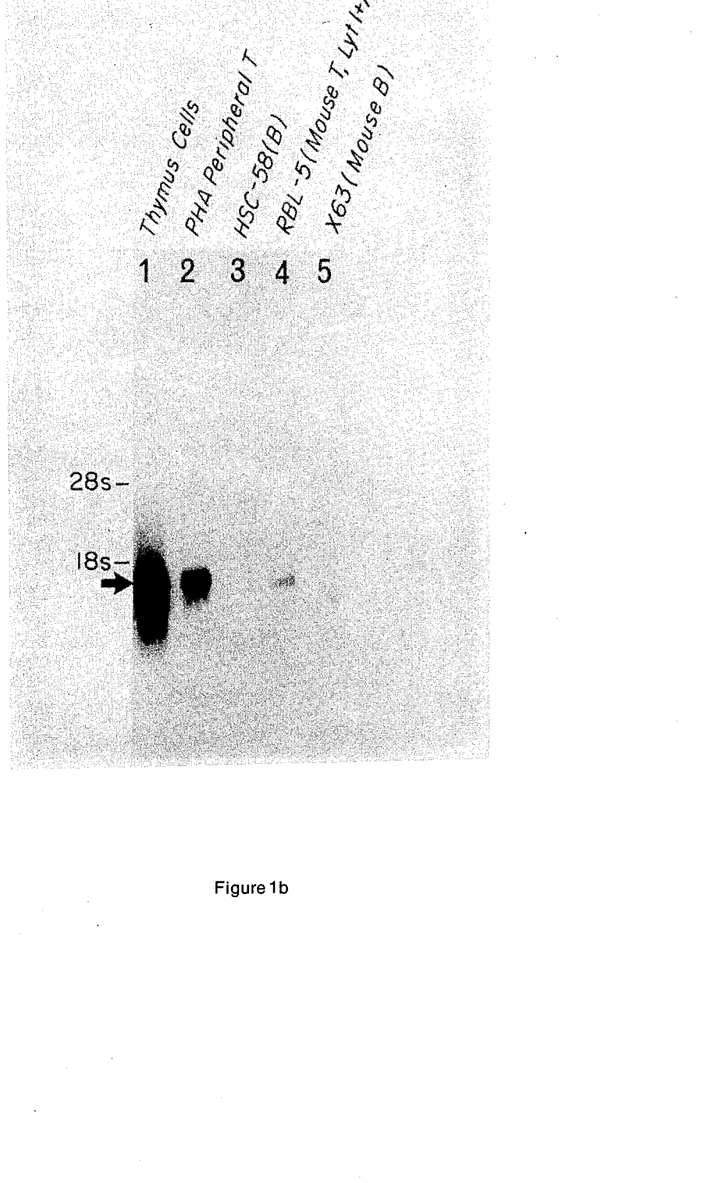

The expression of these messages in other human and mouse T and B cells were also examined by Northern gel analysis. The results which are summarized in FIG. 1b confirm the above result that sequences complementary to these cDNA clones were expressed in MOLT-3 T cells but not in HSC-58 B cells. In addition, the clones were expressed in normal human thymocytes, phytohaemmaglutinin (PHA) stimulated human peripheral blood T cells, and the mouse T cell line RBL-5 (FIG. 1b).

These results indicate that the cDNA clones YT30, YT35, YT53 and YT76 were derived from mRNA common in T cell lines.

Figure 2:
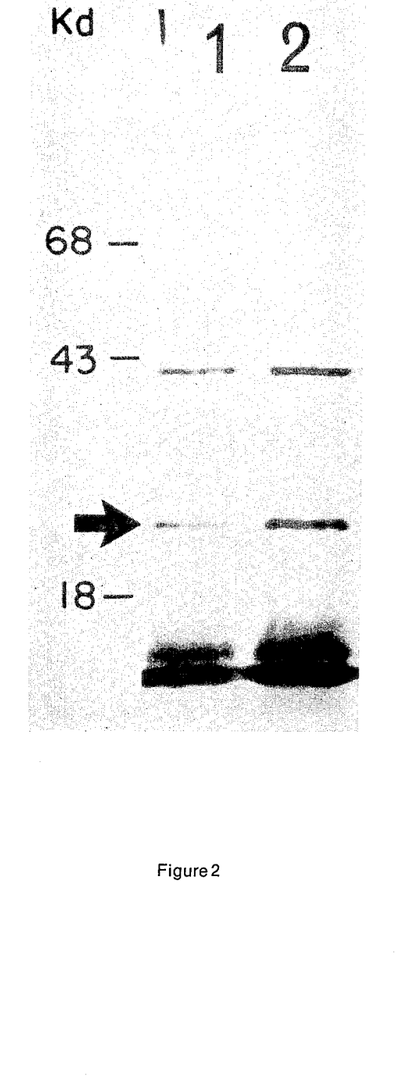
FIG. 2 is a SDS-polyacrylamide gel electrophoresis of the in vitro translation products of mRNA that hybridizes to clones YT35 and YT76.

In order to determine the size of the protein encoded by the mRNA corresponding to the T cell specific cDNA clones, the in vitro hybrid selection method of Parnes et al was used ((1981) Proc. Natl. Acad. Sci. USA 78, 2253–2257). Total mRNA from MOLT-3 was allowed to anneal to clone YT35 or YT76. After one day, the unattached mRNA was removed and the hybridized mRNA was released under low ionic conditions and translated in vitro with a rabbit reticulocyte lysate. The protein synthesized after this hybrid selection method is shown in FIG. 2. The 30,000 dalton protein (arrow) appeared to be coded for by the mRNA selected by the T cell specific cDNA clone, while the larger protein having a molecular weight of about 45,000 daltons was intrinsic to the in vitro translation system.

Figure 3:
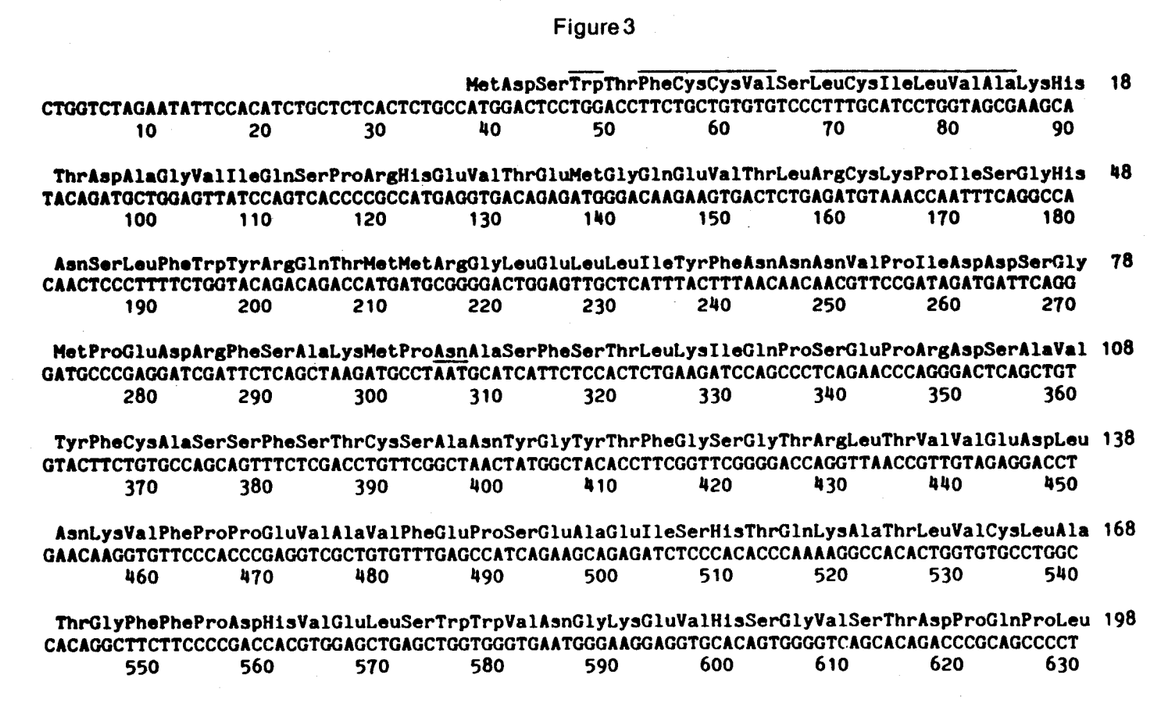
FIGS. 3 and 3a show is a nucleotide and deduced amino acid sequence of a portion of the T cell-specific clone YT35 wherein T represents thymine nucleotide, G represents guanine nucleotide, A represents adenine nucleotide, and C represents cytosine nucleotide.
Figure 3A:
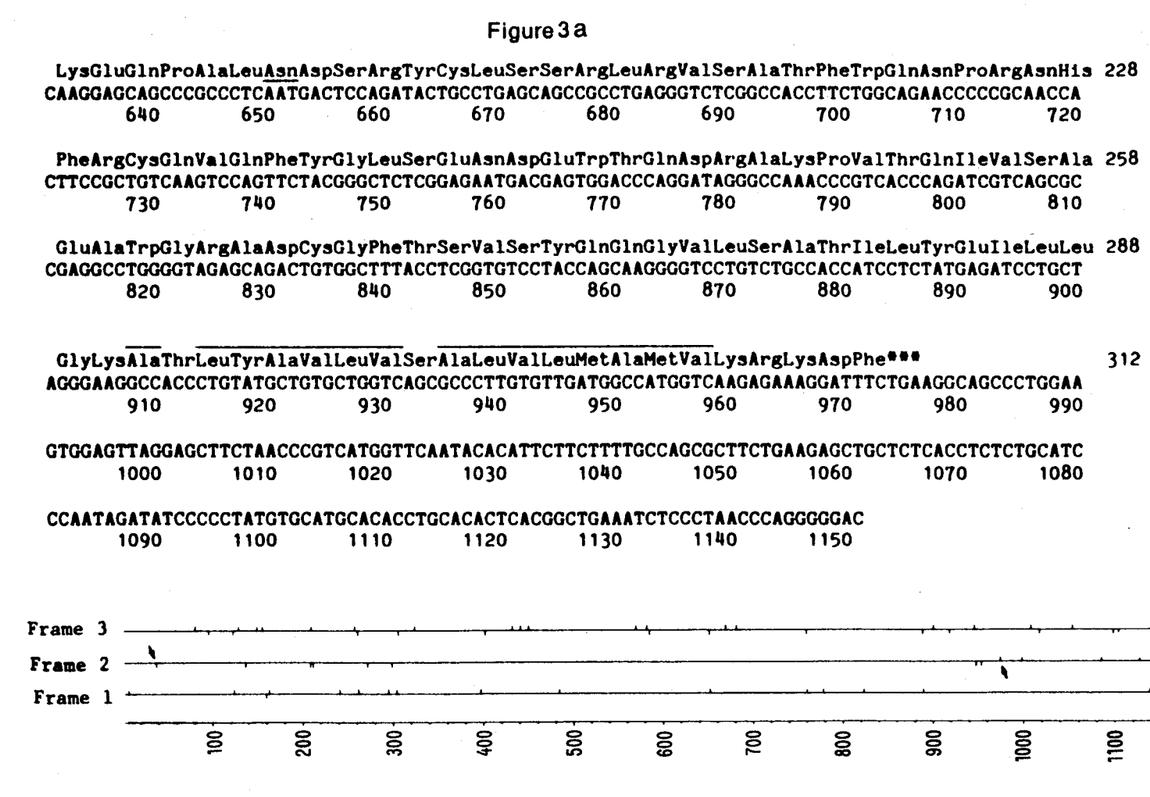

The nucleotide sequence of the YT35 clone was determined using the dideoxy chain terminating inhibitor method of Sanger et al ((1977) Proc. Natl. Acad. Sci. 74, 5463–5467). A complete sequence of 1151 nucleotides is shown in FIGS. 3 and 3a. Examination of this sequence reveals a long open reading frame with a TGA termination triplet at position 974. In the lower portion of FIG. 3 the positions of the methionine codons (bars below line) and termination codons (bars above line) of the three coding frames are shown.

A protein that initiates at the first ATG methionine codon in this reading frame (position 38) has a deduced molecular weight of 34938 daltons, which is in general agreement with the results of hybrid selection and in vitro translation (FIG. 2). There are stretches of nonpolar uncharged amino acids in this protein adjacent the N and C termini (overlining in FIGS. 3 and 3a). The possible sites of N-glycosylation are shown in FIG. 3 by underlining.

Figure 4:
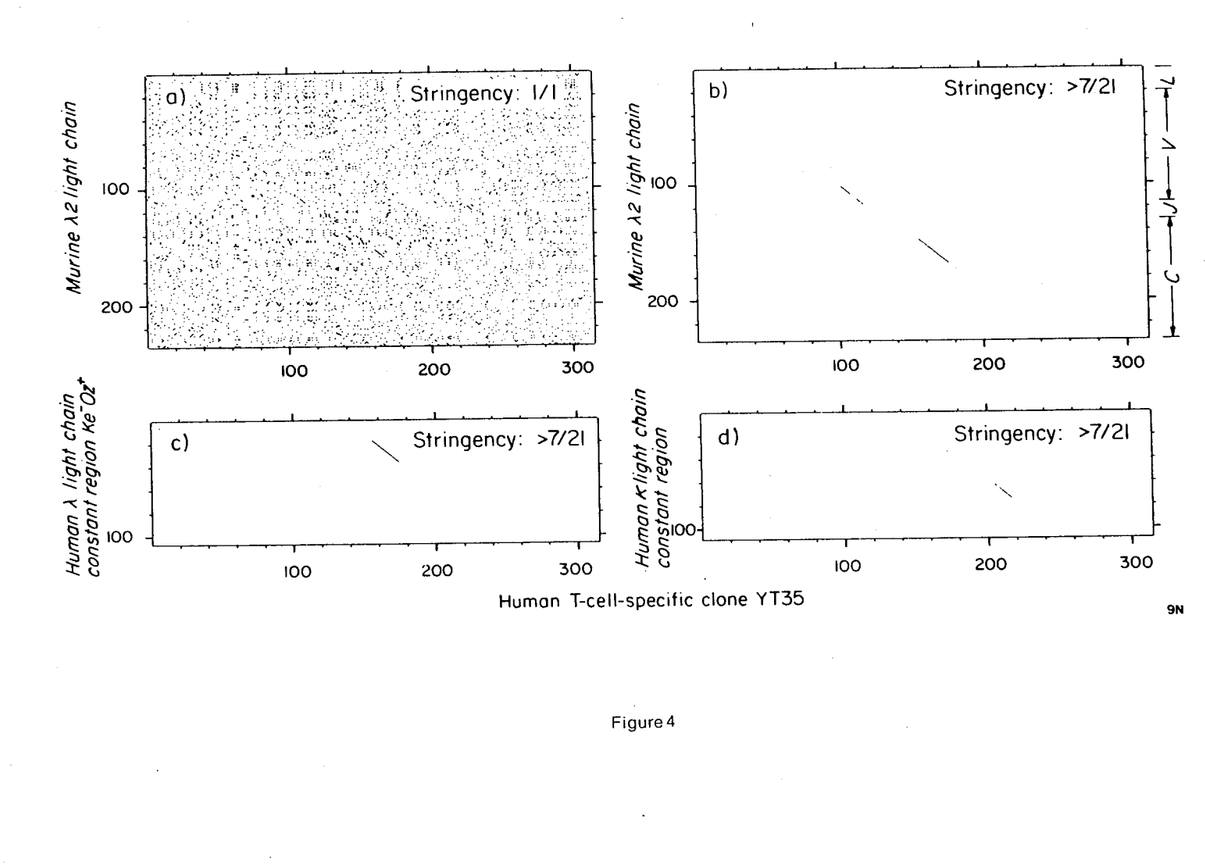
FIG. 4 is a diagonal dot matrix comparison of the deduced amino acid sequence of clone YT35 as shown in FIGS. 3 and 3a, and the amino acid sequences of mouse and human light chains.
Figure 5:
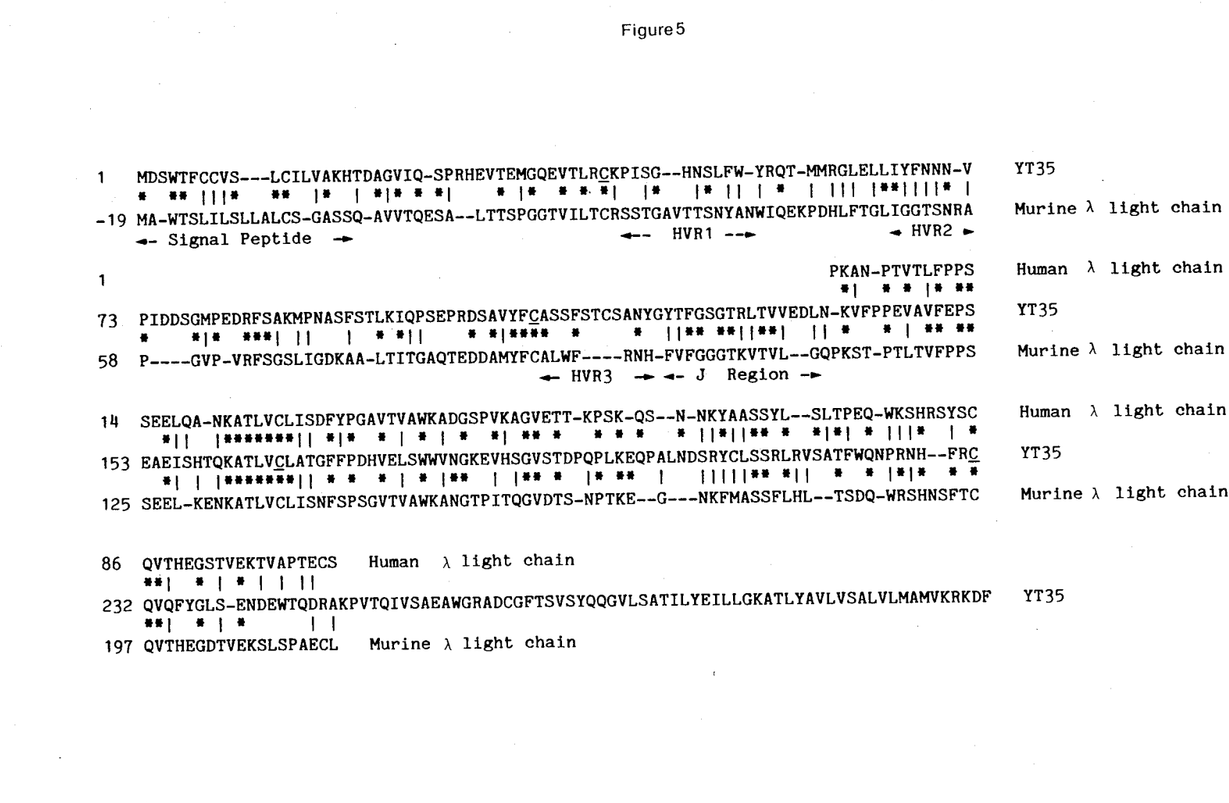
FIG. 5 a direct comparison of the deduced amino acid sequence of clone YT35 as shown in FIGS. 3 and 3a, and those of mouse and human λ light chains.

In order to determine if the deduced amino acid sequence of the T cell specific clone is similar to any of the immunoglobulin or T cell-related protein sequences, these proteins were surveyed by diagonal dot-matrix analysis (FIG. 4). It was found that a long region of homology was perceptible between the protein sequences deduced from clone YT35 and a mouse λ light chain (FIG. 4a) and human λ and K light chains. This homology is more easily recognized when the background is reduced by looking for >35% homology over 21 contiguous amino acids. The resulting plots (FIGS. 4b, c and d) show that there are two stretches with high homology, one near the C-terminal side of the variable region and the other near the N-terminal side of the constant region. A direct comparison of these sequences is shown in FIG. 5. The cysteine residues at positions 42, 111, 166 and 231 of YT35 are underlined. Identity between the sequences is shown with asterisks (*) and vertical lines (|) denote conservative changes. Gaps (—) were introduced to increase the matchup. To identify conservative changes, the amino acids were grouped as follows—Acidic: aspartic acid (D) and glutamic acid (E); basic: histidine (H), lysine (K) and arginine (R); uncharged polar: asparagine (N), glutamine (Q), serine (S) and threonine (T); and nonpolar: alanine (A), cysteine (C), phenylalanine (F), glycine (G), isoleucine (I), leucine (L), methionine (M), proline (P), valine (V), tryptophan (W) and tyrosine (Y). The highest homology that was detected in FIG. 4 corresponds to the region surrounding the cysteine residues at positions 111 and 166 in the YT35 sequence. The sequences are quite similar near the cysteine residue at positions 42 and 231 as well. FIG. 5 also emphasizes the homology that was detected along the entire YT35 protein in FIG. 4a. A comparison of the deduced amino acid sequence of clone YT35 to a human K light chain protein showed slightly lower, but easily detectable, homology than to the λ light chains (not shown). Less pronounced homology was found to a heavy chains of human or mouse immunoglobulins, but no significant homology was found to mouse H-2, Thy-1 or human HLA. The overall homology along the stretch of 249 amino acids that overlaps with the λ light chains is 33% identical to the mouse λ light chain and 38% in the constant region. As well, the homology increases to 59% and 58% respectively if one takes into consideration conservative changes. The respective homology to the constant region of human λ light chain is similar, at 36% identity and 61% with conservative changes. It is of interest to note that the protein encoded by clone YT35 is equally similar to the human and mouse light chains, and that the similarity is highest where the human and mouse light chains are most conserved between themselves. Also, the highest homology to the λ and K chains occurs at different positions (FIG. 4).

The foregoing results indicate two important findings. First, a human T cell-specific cDNA clone has been isolated, and second, it has been determined that the protein, as deduced from the nucleotide sequence, resembles human and mouse immunoglobulin light chain molecules as being similar in the relative locations of the cysteine residues, but more importantly, extensive homology to the variable, joining, and constant regions can be found. These structural features indicate to one of ordinary skill that the protein encoded by YT35 is part of the antigen receptor that mediates specialized T lymphocyte function.

A nucleic acid sequence of at least about 936 nucleotides encodes a polypeptide which is at least part of a T cell antigen receptor, e.g., a primate T cell antigen receptor, preferably a human T cell antigen receptor. The nucleic acid may be DNA, e.g., cDNA, or RNA. One such DNA sequence is shown in part in FIGS. 3 and 3a. Other such DNA sequences contain at the 5' end at least about a 174 base sequence identical to the sequence shown in FIG. 3 at positions 973 to 800. One such RNA sequence is a sequence complementary to that shown in FIGS. 3 and 3a. Other such RNA sequences contain at the 3' end at least about a 174 base sequence complementary to the sequence shown in FIGS. 3 and 3a at positions 973 to 800.

The nucleic acid sequences may be used as probes if labeled with a detectable marker, e.g., a radioactive, fluorescent or biotinylated marker. Labeled probe nucleic acid sequences according to the invention may be used, inter alia, to determine whether an unknown cell, e.g., a tumor cell, is a T cell.

A cDNA sequence according to the invention may be prepared as follows. Total messenger RNA (mRNA) is obtained from a T cell, e.g., a MOLT-3 cell or a thymocyte and used to prepare cDNA complementary to the mRNA. The cDNA is inserted into an appropriate cloning vehicle, e.g., pBR322 or pFP502EBS, which is then inserted into a suitable host, e.g., E. coli. The resulting host is cultured under appropriate conditions permitting production of multiple copies of the cDNA, and the cDNA so produced is recovered and screened to determine whether it is expressed only in T cells.

Host cells containing a suitable cloning vehicle which includes cDNA encoding the T cell antigen receptor may be prepared and used to produce the receptor polypeptide in accordance with methods known to those of ordinary skill in the art.

The invention also concerns polypeptides encoded by the nucleic acid sequences including a polypeptide which is at least part of a T cell antigen receptor and contains at least about 312 amino acids as shown in FIGS. 3 and 3a. Other polypeptides of at least about 312 amino acids which contain at the C-terminus at least about 58 amino acids identical to the sequence shown in FIGS. 3 and 3a at positions 255 to 312 are T cell receptor antigens. Such polypeptides include at least one sequence which over 21 contiguous amino acids has greater than about 35% homology with mouse and human λ light chains, such homology being present with sequences in the variable, joining and constant regions.

Antibodies to the polypeptides, e.g., monoclonal or serum-derived antibodies, may be prepared using methods known to those skilled in the art. Such antibodies may be employed to detect the presence of T cell receptor antigen and to determine whether an unknown cell, e.g., a tumor cell, is a T cell. To do so the sample to be tested is treated with the antibody under suitable conditions permitting formation of antigen antibody complex and a determination made whether complex is present.

We claim:

1. An isolated nucleic acid sequence encoding a polypeptide which is at least part of the beta chain of a human T cell antigen receptor comprising at least about 936 nucleotides.

2. A nucleic acid of claim 1, wherein the nucleic acid is DNA.

3. A nucleic acid of claim 2, wherein the nucleic acid is a cDNA.

4. A nucleic acid of claim 1, wherein the nucleic acid is RNA.

5. A nucleic acid of claim 2 containing at the 5' end at least about a 174 nucleotide sequence identical to the sequence of YT35 at positions 973 to 800.

6. A nucleic acid of claim 4 containing at the 3' end at least about a 174 nucleotide sequence complementary to the sequence of YT35 at positions 973 to 800.

7. A nucleic acid of claim 2 having the sequence of YT35.

8. A substantially pure DNA sequence being approximately 60% or more homologous with the clone YT35 as measured by hybridization therewith.

9. A nucleic acid of claim 1 labeled with a detectable marker.

10. A nucleic acid of claim 9, wherein the marker is radioactive.

11. A nucleic acid of claim 9, wherein the marker is fluorescent.

12. A nucleic acid of claim 9, wherein the marker is biotinylated.

13. A method of preparing the cDNA of claim 3 which comprises obtaining mRNA from a human T cell, preparing cDNA complementary to the mRNA, inserting the cDNA into an appropriate cloning vehicle, introducing the cloning vehicle into a suitable host, culturing the resulting host under appropriate conditions permitting production of multiple copies of the cDNA, recovering the cDNA so produced and screening the cDNA to determine whether said cDNA is expressed only in T cells.

14. A method of claim 13, wherein the T cell is an MOLT-3 cell.

15. A method of claim 13, wherein the T cell is a thymocyte.

16. A method of claim 13, wherein the cloning vehicle is pBR322.

17. A method of claim 13, wherein the suitable host is E. coli.

18. A cloning vehicle comprising the nucleic acid of claim 1.

19. A cloning vehicle comprising the nucleic acid of claim 3.

20. A cloning vehicle comprising the nucleic acid of claim 8.

21. A host cell comprising the cloning vehicle of claim 18.

22. A microorganism comprising the cloning vehicle of claim 18.

23. A microorganism comprising the cloning vehicle of claim 20.

24. A method of producing a polypeptide which is at least part of a human T cell antigen receptor which comprises introducing the cloning vehicle of claim 18 into a suitable host, culturing the resulting host under appropriate conditions permitting expression of the polypeptide and recovering the polypeptide so expressed.

* * * * *